(12) United States Patent
Chulay

(10) Patent No.: US 6,413,993 B1
(45) Date of Patent: Jul. 2, 2002

(54) COMBINATION PREPARATION FOR TREATING MALARIA

(75) Inventor: Jeffrey David Chulay, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/958,402
(22) PCT Filed: Apr. 5, 2000
(86) PCT No.: PCT/US00/09091
§ 371 (c)(1), (2), (4) Date: Oct. 9, 2001
(87) PCT Pub. No.: WO00/61133
PCT Pub. Date: Oct. 19, 2000

Related U.S. Application Data

(60) Provisional application No. 60/128,672, filed on Apr. 9, 1999.

(51) Int. Cl.$^7$ ................................................ A61K 31/15
(52) U.S. Cl. ................. 514/350; 514/565; 514/682; 514/892
(58) Field of Search ................. 514/350, 565, 514/682, 895

(56) References Cited

U.S. PATENT DOCUMENTS 6,291,488 B1 * 9/2001 Gutteridge et al. ......... 514/350

FOREIGN PATENT DOCUMENTS

WO 94/12164 6/1994

OTHER PUBLICATIONS

Srivastava, Antimicrob. Agents Chemothwer, vol. 43(6) pp. 1334–1339 (abstract) 1999.*
Kremsner et al, J. Travel Medicine, vol. 6, suppl. 1(abstract), May 1999.*
Looareesauwan et al, Trans R Soc Trop Med Hy, vol. 93(6) pp. 637–640 (abstract), Nov.–Dec. 1999.*
Looareesuwan, S. et al., "Clinical Studies of Atovaquone, Alone of in Combination with Other Antimalarial Drugs, for Treatment of Acute Uncomplicated Malaria in Thailand," American Journal of Tropical Medicine & Hygiene, vol. 54, No. 1, Jan. 1996, pp. 62–66.
Cedillos, R.A. et al., "Field Evaluation of Primaquine in the Control of Plasmodium–Vivax,", American Journal of Tropical Medicine & Hygiene, vol. 27, No. 3, 1978, pp. 466–472.
Srivastava, H.C. et al., "Studies on Plasmodium vivax relapse pattern in Kheda District, Gujarat," Indian Journal of Malariology, vol. 33, No. 4, 1996, pp. 173–179.

* cited by examiner

Primary Examiner—James H. Reamer
(74) Attorney, Agent, or Firm—Bonnie L. Deppenbrock

(57) ABSTRACT

Methods of treatment and prevention of malarial infection caused by *Plasmodium vivax*, in which combinations of atovaquone, proguanil and primaquine are administered to a patient.

15 Claims, No Drawings

COMBINATION PREPARATION FOR TREATING MALARIA

This application is filed pursuant to 35 U.S.C. §371 as a United States National Phase Application of International Application No. PCT/US00/09091 filed Apr. 5, 2000, which claims priority from 60/128,672 filed Apr. 9, 1999.

The resent invention relates to combinations of atovaquone {2-[4-(4-chlorophenyl) cyclohexyl]-3-hydroxy-1,4-naphthoquinone}, proguanil {1-(4-chlorophenyl)-5-isopropylbiguanide hydrochloride} and primaquine {(RS)-8-(4-amino-1-methylbutylamino)-6-methoxyquinoline diphosphate} which have anti-malarial activity. More specifically, the invention is concerned with the use of such combinations in the treatment and prophylaxis of *Plasmodium vivax* malaria.

The combination of atovaquone and proguanil for the treatment of malaria has previously been disclosed in, for example, international patent application WO9412164, the entire disclosure of which is incorporated herein by reference. The combination of atovaquone and proguanil is commercially available under the name Malarone (Registered Trade Mark of the Glaxo Wellcome group of companies) as a fixed dose combination containing 250 mg of atovaquone and 100 mg proguanil.

In order to combat drug resistance and to improve antimalarial chemotherapy, it is becoming standard practice to use combinations of more than one antimalarial, either simultaneously or sequentially. However, many such combinations are antagonistic, resulting in less effective treatment and the dosage regimens are often complicated, increasing the likelihood of patients failing to complete the treatment. Moreover, there are four species of human malaria parasites each of which may react differently to any combination of antimalarial drugs. In particular, *P. vivax* malaria is difficult to treat successfully because a latent form of the parasite persists in the liver after treatment with most anti-malarial drugs.

It has now surprisingly been found that by combining atovaquone, proguanil and primaquine potentiation of antimalarial activity is achieved. The invention is particularly suited to the treatment and/or prophlyaxis of *P. vivax* malaria In a first aspect, the present invention provides a method for the treatment and/or prophylaxis of malaria, particularly *P. vivax* malaria, in mammals, including humans, which comprises administering a therapeutically effective amount of atovaquone and concomitantly or sequentially administering a therapeutically effective amount of proguanil and concomitantly or sequentially administering a therapeutically effective amount of primaquine.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

Preferably, atovaquone and proguanil are administered concomitantly and primaquine is administered subsequently. More preferably atovaquone and proguanil are administered concomitantly in the ratio 5:2 followed by administration of primaquine. Most preferably atovaquone and proguanil are administered as the fixed dose combination Malarone followed by administration of primaquine.

Thus, in a preferred embodiment the present invention provides a method for the treatment and/or prophylaxis of malaria, particularly *P. vivax* malaria, in mammals, including humans, which comprises administering concomitantly a therapeutically effective amount of atovaquone and proguanil in the ratio 5:2 and sequentially administering a therapeutically effective amount of primaquine.

In a second aspect, the present invention provides the use of atovaquone for the manufacture of a medicament, for administration, either sequentially or concomitantly, with proguanil and primaquine, for the treatment and/or prophylaxis of malaria, particularly *P. vivax* malaria, in mammals, including humans.

In another aspect, the present invention provides the use of atovaquone and proguanil for the manufacture of a medicament for administration sequentially with primaquine, for the treatment and/or prophylaxis of malaria, particularly *P. vivax* malaria, in mammals, including humans.

In a preferred embodiment of this aspect, the present invention provides the use of atovaquone and proguanil in the ratio 5:2 for the manufacture of a medicament for administration sequentially with primaquine, for the treatment and/or prophylaxis of malaria, particularly *P. vivax malaria*, in mammals, including humans.

in a further aspect, the present invention provides the use of atovaquone, proguanil and primaquine for the manufacture of a medicament for treatment and/or prophylaxis of malaria, particularly *P. vivax* malaria, in mammals, including humans.

Conveniently atovaquone, proguanil and primaquine are administered concomitantly. Preferably, atovaquone, proguanil and primaquine are administered in a potentiating ratio.

Thus, according to another aspect of the present invention there is provided a combination of atovaquone, proguanil and primaquine wherein the atovaquone, proguanil and primaquine are present in a potentiating ratio.

The term 'potentiating ratio' is-used herein to indicate that atovaquone, proguanil and primaquine are present in a ratio such that the antimalarial activity of the combination is greater than that of either atovaquone, proguanil or primaquine alone or of the additive activity that would be predicted for the combination based on the activities of the individual components. Thus the individual components act synergistically in combination provided they are present in a potentiating ratio.

A potentiating ratio, which may be successfully used to treat malaria, particularly *P. vivax* malaria, is in the range 1–250:1–1000:1 of proguanil:atovaquone:primaquine. Suitably, the potentiating ratio is in the range 2–100:5–200:1. A particularly preferred potentiating ratio is in the range 4-30:10–75:1 .

According to a still further aspect of the present invention, there is provided a kit comprising in association for separate administration atovaquone, proguanil and primaquine. Preferably, the kit comprises atovaquone and proguanil in the ratio 5:2 and primaquine. Most preferably, the kit comprises Malarone and primaquine.

The amount of a combination of atovaquone, proguanil and primaquine required to be effective as an antimalarial agent will, of course, vary and is ultimately at the discretion of the medical or veterinary practitioner. The factors to be considered include the route of administration and nature of the formulation, the mammal's bodyweight, age and general condition and the nature and severity of the disease to be treated. In general, a suitable effective dose for administration to man for treatment of malaria is in the range of 0.2 to 20 mg of proguanil per kilogram bodyweight per day, 2.0 mg to 100 mg of atovaquone per kilogram bodyweight per day and 0.05 mg to 10 mg of primaquine per kilogram bodyweight per day, for example from 0.5 to 15 mg/kg/day of proguanil, 4 to 50 mg/kg/day of atovaquone and 0.1mg to 5 mg/kg/day of primaquine, particularly 3 to 10 mg/kg/day of proguanil, 10 to 25 mg/kg/day of atovaquone and 0.2 to 2 mg/kg/day of primaquine. Preferably, atovaquone and proguanil are administered concomitantly for three days and primaquine is administered alone for 14 days.

A suitable effective dose for administration to man for prophylaxis of malaria is in the range of from 0.05 to 20 mg of proguanil per kilogram bodyweight per day, 0.2 to 50 mg of atovaquone per kilogram bodyweight per day and 0.05 to 10 mg of primaquine per kilogram bodyweight per day, for example from 0.1 to 10 mg/kg/day of proguanil, 0.5 to 20 mg/kg/day of atovaquone and 0.1 to 5 mg/kg/day of primaquine, particularly 0.5 to 5 mg/kg/day of proguanil, 1 to 10 mg/kg/day of atovaquone and 0.2 to 2 mg/kg/day of primaquine. Preferably, atovaquone and proguanil are administered concomitantly during exposure to malaria and for a further 7 days after exposure has ended, and primaquine is administered for 14 days after exposure to malaria has ended.

It should be understood that the dosages referred to above are calculated in terms of the drugs per se.

For use according to the present invention the combination of atovaquone, proguanil and primaquine is preferably presented as a pharmaceutical formulation.

Pharmaceutical formulations comprise the active ingredients (that is, the combination of atovaquone, proguanil and primaquine) together with one or more pharmaceutically acceptable carriers therefor and optionally other therapeutic and/or prophylactic ingredients. The carrier(s) must be acceptable in the sense of being compatible with the other ingredients of the formula and not deleterious to the recipient thereof.

Accordingly, the present invention provides a pharmaceutical formulation comprising a combination of atovaquone, proguanil and primaquine in association with one or more pharmaceutically acceptable carriers thereof. Preferably, the combination of atovaquone, proguanil and primaquine are in a potentiating ratio.

The present invention further provides a process for the preparation of a pharmaceutical formulation which process comprises bringing into association a combination of atovaquone proguanil and primaquine with one or more pharmaceutically acceptable carriers therefor.

The combination of atovaquone and proguanil may conveniently be presented as a pharmaceutical formulation in unit dosage form. A convenient unit dose formulation contains the active ingredients in amounts of from 5 mg to 3 g each, e.g. 25 mg to 2 g each. Typical unit doses may contain for example 500 mg of atovaquone, 200 mg of proguanil and 15 mg of primaquine. Pharmaceutical formulations include those suitable for oral, topical (including dermal, buccal and sublingual), rectal and parenteral (including subcutaneous, intradermal, intramuscular and intravenous), administration as well as administration by naso-gastric tube. The formulation may, where appropriate, be conveniently presented in discrete dosage units and may be prepared by any of the methods well known in the art of pharmacy. All methods include the step of bringing into association the active ingredients with liquid. carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of the active ingredients. A tablet may be made by compression or molding, optionally with one or more accessory ingredients. Compressed tablets may be prepared by compressing in a suitable machine the active compounds in a free-flowing form such as a powder or granules optionally mixed with a binder, lubricant, inert diluent, lubricating agent, surface-active agent or dispersing agent. Molded tablets may be made by molding an inert liquid diluent. Tablets may be optionally coated and, if uncoated, may optionally be scored. Capsules may be prepared by filling the active ingredients, either alone or in admixture with one or more accessory ingredients, into the capsule shells and then sealing them in the usual manner. Cachets are analogous to capsules wherein the active ingredients together with any accessory ingredient(s) are sealed in a rice paper envelope. The combination of atovaquone, proguanil and primaquine may also be formulated as dispersible granules, which may for example be suspended in water before administration, or sprinkled on food. The granules may be packaged e.g. in a sachet. Formulations suitable for oral administration wherein the carrier is a liquid may be presented as a solution or a suspension in an aqueous liquid or a non-aqueous liquid, or as an oil-in-water liquid emulsion.

Formulations for oral. administration include controlled release dosage forms e.g. tablets wherein the active ingredients are formulated. in an appropriate release—controlling matrix, or are. coated with a suitable release—controlling film. Such formulations may be particularly convenient for prophylactic use.

The active ingredients may also be formulated as a solution or suspension suitable for administration via a naso-gastric tube.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in moulds.

Pharmaceutical formulations suitable for parenteral administration include sterile solutions or suspensions of the active combination in aqueous or oleaginous vehicles. Injectable preparations may be adapted for bolus injection or continuous infusion. Such preparations are conveniently presented in unit dose or multi-dose containers which are sealed after introduction of the formulation until required for use. Alternatively, the active ingredients may be in powder form which are constituted with a suitable vehicle, such as sterile, pyrogen-free water, before use.

The combination of atovaquone and proguanil may also be formulated as a long-acting depot preparation, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

It should be understood that in addition to the aforementioned carrier ingredients the pharmaceutical formulations for the various routes of administration described above may include, as appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Compositions suitable for veterinary use include those adapted for oral, parenteral, and intrarumenal administration.

Methods for preparing atovaquone are described in European patent no. 123,238, the entire disclosure of which is incorporated herein by reference.

BIOLOGICAL DATA 45 adults with acute manifestations of malaria (e.g. fever) and asexual *vivax parasitemia* greater than 40 parasites/$\mu$l were treated with 1000 mg atovaquone and 400 mg proguanil hydrochloride on 3 consecutive days followed by 30 mg primaquine daily for 14 days.

35 of the 45 subjects completed the 12-week follow-up period. 33 (94%) had an adequate clinical response. 2 subjects (6%) recrudesced on day 56 and were considered late stage treatment failures.

Median parasite clearance time was 88h; median fever clearance time was 34h.

The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims.

What is claimed is:

1. A method for the treatment and/or prophylaxis of malaria, particularly *P. vivax* malaria, in mammals, including humans, which comprises administering a therapeutically effective amount of atovaquone and concomitantly or sequentially administering a therapeutically effective amount of proguanil and concomitantly or sequentially administering a therapeutically effective amount of primaquine.

2. A combination of atovaquone, proguanil and primaquine wherein the atovaquone, proguanil and primaquine are present in a potentiating ratio.

3. A kit comprising in association for separate administration atovaquone, proguanil and primaquine.

4. A pharmaceutical formulation comprising a combination of atovaquone, proguanil and primaquine in association with one or more pharmaceutically acceptable carriers thereof.

5. The method of claim 1 wherein atovaquone and proguanil are adminstered concomitantly and primaquine is administered subsequently.

6. The method of claim 1 wherein atovaquone, proguanil and primaquine are administered concomitantly.

7. The method of claim 1 wherein the ratio of atvaquone and proguanil is 5:2.

8. The method of claim 1 wherein atovaquone, proguanil and primaquine are administered in a potentiating ratio.

9. The method of claim 10 wherein the potentiating ratio of proguanil:atovaquone:primaquine is in the range of 1–250:1–1000:1.

10. The method of claim 9 wherein the potentiating ratio is 2-100:5–200:1.

11. The combination of claim 2 wherein the potentiating ratio of proguanil:atovaquone:primaquine is in the range of 1–250:1–1000:1.

12. The combination of claim 11 wherein the range of the potentiating ratio is 2–100:5–200:1.

13. The kit of claim 3 wherein the ratio of atovaquone and proguanil is 5:2.

14. The pharmaceutical formulation of claim 4 wherein atovaquone, proguanil and primaquine are in a potentiating ratio of proguanil:atovaquone:primaquine in the range of 1–250:1–1000:1.

15. The pharmaceutical formulation of claim 14 wherein the range of the potentiating ratio is 2–100:5–200:1.

* * * * *